United States Patent
Basu et al.

(10) Patent No.: US 8,081,733 B2
(45) Date of Patent: Dec. 20, 2011

(54) METHOD AND SYSTEMS FOR SCANNING A STREAM OF OBJECTS

(75) Inventors: Samit Kumar Basu, Fremont, CA (US);
Pierfrancesco Landolfi, Palo Alto, CA (US); Eugene Alex Ingerman, Newark, CA (US); Jian Gao, Newark, CA (US); Mikhail Kourinny, Newark, CA (US)

(73) Assignee: Morpho Detection, Inc., Newark, CA (US)

( * ) Notice: Subject to any disclaimer, the term of this patent is extended or adjusted under 35 U.S.C. 154(b) by 250 days.

(21) Appl. No.: 12/391,470

(22) Filed: Feb. 24, 2009

(65) Prior Publication Data

US 2010/0215143 A1     Aug. 26, 2010

(51) Int. Cl.
*G01N 23/00* (2006.01)
(52) U.S. Cl. .............................................. 378/19; 378/4
(58) Field of Classification Search .................. 378/4, 8, 378/19, 62, 901, 20; 382/131, 132
See application file for complete search history.

(56) References Cited

U.S. PATENT DOCUMENTS

| | | | |
|---|---|---|---|
| 5,901,198 A | 5/1999 | Crawford et al. | |
| 5,949,842 A | 9/1999 | Schafer et al. | |
| 5,970,113 A | 10/1999 | Crawford et al. | |
| 6,185,272 B1 | 2/2001 | Hiraoglu et al. | |
| 6,256,404 B1 | 7/2001 | Gordon et al. | |
| 6,430,255 B2 | 8/2002 | Fenkart et al. | |
| 7,050,536 B1 | 5/2006 | Fenkart et al. | |
| 7,203,267 B2 | 4/2007 | De Man et al. | |
| 7,453,980 B1 * | 11/2008 | Gilevich et al. | 378/57 |

* cited by examiner

*Primary Examiner* — Jurie Yun
(74) *Attorney, Agent, or Firm* — Armstrong Teasdale LLP

(57) ABSTRACT

A method for scanning a stream of objects includes continuously acquiring raw data of the stream of objects using an X-ray system including a detector, determining a leading edge and a trailing edge of a first object of the stream of objects from the raw data acquired by the detector using a control system, processing acquired raw data of the first object based on the determined leading edge and the determined trailing edge using the control system, and reconstructing an image of the first object using at least the processed raw data. A system configured to perform the method is also disclosed.

20 Claims, 3 Drawing Sheets

METHOD AND SYSTEMS FOR SCANNING A STREAM OF OBJECTS

BACKGROUND OF THE INVENTION

1. Field of the Invention

The embodiments described herein relate generally to tomographic systems, such as computed tomography (CT) systems, and, more particularly, to CT systems that scan a continuous stream of objects.

2. Description of the Related Art

At least some known tomographic systems scan a continuous stream of objects. In such tomographic systems, it is generally necessary to partition data generated by the tomographic system into blocks associated with each object in the stream of objects. For such tomographic systems to perform partitioning of the data successfully, the tomographic system determines an extent of each object and completes data acquisition for each object as each object passes through the tomographic system. As used herein, the term "extent of an object" refers to the physical boundaries, dimensions, and/or measurements of the object, such as the physical volume of the object, and/or data representing the physical object. In at least one known tomographic system, a machine control for a scanning device generally includes information about each object from an external system that transports the objects into a scanning device, such as a CT system. One such external system includes passive curtains to determine the extent of each object. However, objects passing through the passive curtains may be repositioned, such as "joining up" or shifting orientation, before and/or inside the scanning device. Such repositioning may cause confusion between the extent of an object as externally measured, and the extent of the object once inside the scanning device. As such, there is a need to determine extents of objects within the scanning device.

In at least some known tomographic systems for scanning a stream of objects, the reconstruction subsystem, which generates high resolution images, cannot keep pace with the data acquisition of the scanning device. Such tomographic systems rely on gaps between the objects within the stream to catch up to a flow of objects. More specifically, during the gaps, the tomographic system can process data of one object before data for the next object in the stream is acquired. As such, there is a need to collect data only during the physical extent of the objects and not during the intervening gaps.

BRIEF SUMMARY OF THE INVENTION

In one aspect, a method for scanning a stream of objects is provided. The method includes continuously acquiring raw data of the stream of objects using an X-ray system including a detector, determining a leading edge and a trailing edge of a first object of the stream of objects from the raw data acquired by the detector using a control system, processing acquired raw data of the first object based on the determined leading edge and the determined trailing edge using the control system, and reconstructing an image of the first object using at least the processed raw data.

In another aspect, a scanning system is provided. The scanning system includes a conveyor configured to transport a stream of objects through the scanning system, and a computer tomography (CT) system configured to generate an image of a first object of the stream of objects. The CT system includes a detector and a control system. The control system is configured to determine a leading edge and a trailing edge of the first object using raw data acquired by the detector, process raw data of the first object based on the determined leading edge and the determined trailing edge, and reconstruct the image of the first object using at least the processed raw data.

In yet another aspect, a computer tomography (CT) system is provided. The CT system includes a radiation source, a detector configured to detect radiation emitted from the radiation source, an examination space defined between the radiation source and the detector, and a control system that includes an object detection subsystem configured to determine a leading edge and a trailing edge of a first object of the stream of objects using raw data acquired by the detector, an acquisition subsystem configured to process raw data of the first object based on the determined leading edge and the determined trailing edge, and a reconstruction subsystem configured to reconstruct an image of the first object using at least the processed raw data.

The embodiments described herein use a CT system to determine leading and trailing edges of each object in a stream of objects being scanned by the CT system. Accordingly, edges and/or boundaries of objects within the CT system are determined, and data is recorded and/or processed when an object is within the CT system and not when an object is not present within the CT system, such as when a gap in the stream of objects is within the CT system.

BRIEF DESCRIPTION OF THE DRAWINGS

FIG. 1 is a schematic view of an exemplary scanning system.

FIG. 2 is a schematic view of an exemplary computer tomography (CT) system that may be used with the scanning system shown in FIG. 1.

FIG. 3 is a flowchart of an exemplary method that may be performed using the scanning system shown in FIG. 1.

DETAILED DESCRIPTION OF THE INVENTION

The embodiments described herein detect a leading edge (LE) and a trailing edge (TE) of each object of a stream of objects through a computer tomography (CT) system to determine when to start and stop recording and/or processing data for each object. As such, a data stream is partitioned to correspond to each object that passes through the CT system. In the embodiments described herein, the LE determination and the TE determination are made directly by the CT system using signals measured on a detector within the CT system. In one embodiment, a control system continuously monitors detector data received by the control system. When an object being scanned enters into an examination space of the CT system, the object creates a signature signal change on the detector. For example, absorption of X-rays by the object will result in a decrease in a number of photons detected by the detector. The control system monitors the detector data for a decrease in signals representative of the decrease in the number of protons detected by the detector.

When the control system detects the decrease in signals, the control system marks current data as indicative of the LE of the object. Buffering views can be used to mark views prior to detection of the LE as part of the object, if necessary. When the detector signal returns to a level present when no object is in the examination space, the control system marks current data as indicative of the TE of the object and terminates recording and/or processing of the received data. Data continues to be acquired and received by the control system, however, such data is not recorded and/or processed. A delay can be used to continue marking views after the detection of the TE as part of the object, if necessary. In a particular embodiment, the control system monitors the detector in multiple sections. More specifically, detector rows that are positioned upstream are used to detect the LE of objects, and detector rows that are positioned downstream are used to detect the TE of objects.

As used herein, the phrase "reconstructing an image" is not intended to exclude embodiments in which data representing an image is generated but a viewable image is not. Therefore, as used herein the term "image" broadly refers to both viewable images and data representing a viewable image. However, many embodiments generate (or are configured to generate) at least one viewable image. Additionally, although described in detail in a CT inspection setting, it is contemplated that the benefits accrue to all imaging modalities including, for example, ultrasound, Magnetic Resonance Imaging, (MRI), Electron Beam CT (EBCT), Positron Emission Tomography (PET), Single Photon Emission Computed Tomography (SPECT), X-ray Tomo-synthesis, and in both non-medical settings and medical settings.

Figure 1:
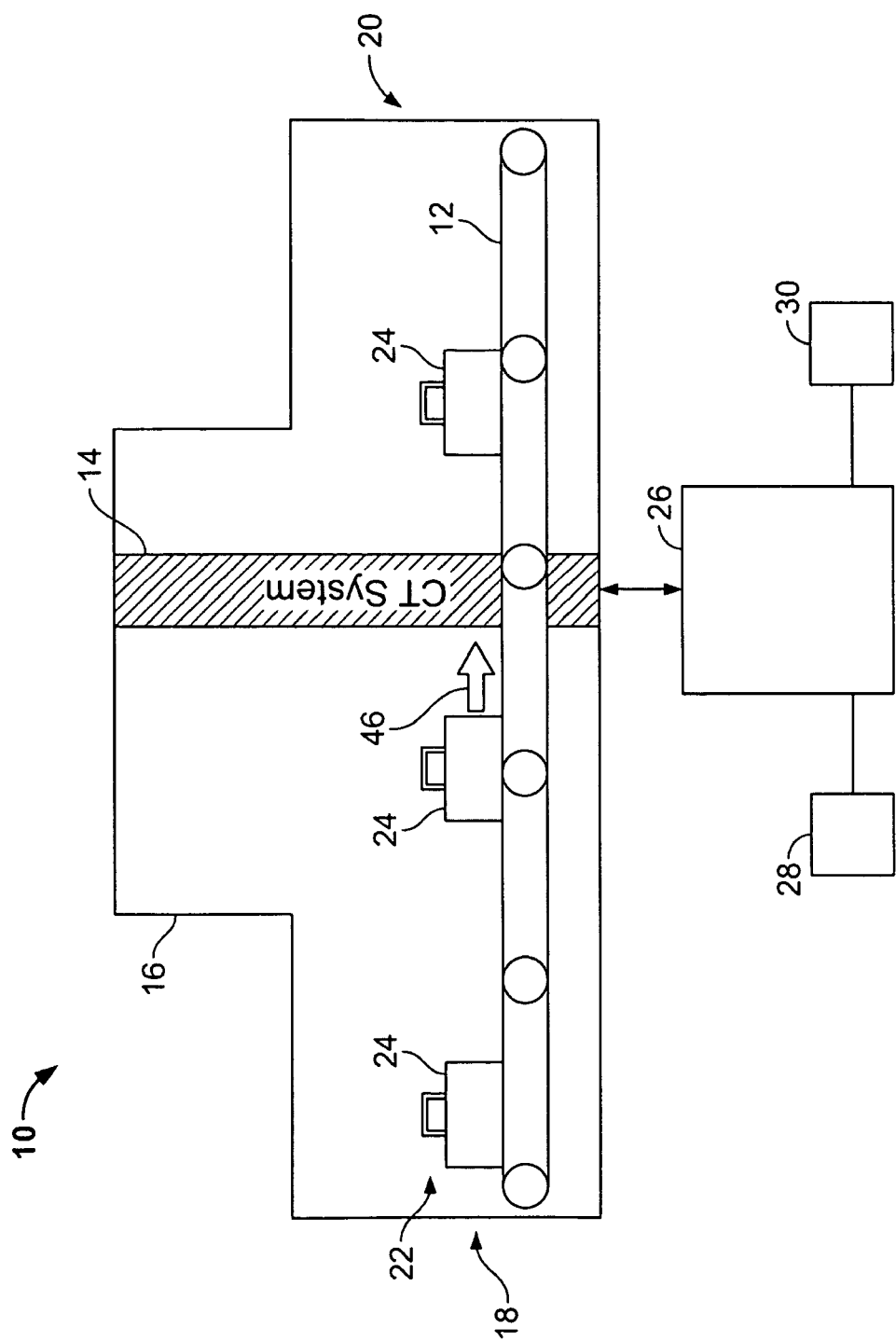
FIGS. 1-3 show exemplary embodiments of the system and method described herein.

FIG. 1 is a schematic view of an exemplary scanning system 10. Scanning system 10 includes a conveyor 12 and a CT system 14 positioned at least partially within a housing 16. Conveyor 12 extends between an inlet 18 of housing 16 and an outlet 20 of housing 16. Further, conveyor 12 is configured to transport a stream 22 of objects 24 through scanning system 10. In the exemplary embodiment, stream 22 includes at least one object 24. Conveyor 12 extends through CT system 14 and conveys objects 24 sequentially through CT system 14 such that each object 24 is scanned by CT system 14. CT system 14 is configured to scan objects 24 one at a time in the exemplary embodiment.

A control system 26 is in operational control communication with conveyor 12 and CT scanner 14. As used herein, "operational control communication" refers to a link, such as a conductor, a wire, and/or a data link, between two or more components of scanning system 10 that enables signals, electric currents, and/or commands to be communicated between the two or more components. The link is configured to enable one component to control an operation of another component of scanning system 10 using the communicated signals, electric currents, and/or commands. Further, as used herein, the term "control system" is not limited to just those integrated circuits referred to in the art as a control system, but broadly refers to a computer, microcontroller, a microcomputer, a programmable logic controller, an application specific integrated circuit, and/or any other programmable circuit.

Control system 26 includes a central processing unit and may include a device, such as a floppy disk drive or a compact-disc read-only memory (CD-ROM) drive, for reading data from a computer-readable medium, such as a floppy disk, a compact disc-read only memory (CD-ROM), a magneto-optical disk (MOD), and/or a digital versatile disc (DVD). In an alternative embodiment, control system 26 executes instructions stored in firmware. In the exemplary embodiment, control system 26 controls speed, acceleration, deceleration, starting, stopping, and/or any other suitable functions of conveyor 12. Moreover, control system 26 controls CT system 14 and/or conveyor 12 to acquire data relating to objects 24, as described in more detail below. In the exemplary embodiment, control system 26 is also in communication with an input device 28 and a display device 30. Display device 30 may include, without limitation, a liquid crystal display (LCD), a cathode ray tube (CRT), and/or any other suitable output device. Input device 28 includes, without limitation, a mouse and a keyboard.

Figure 2:
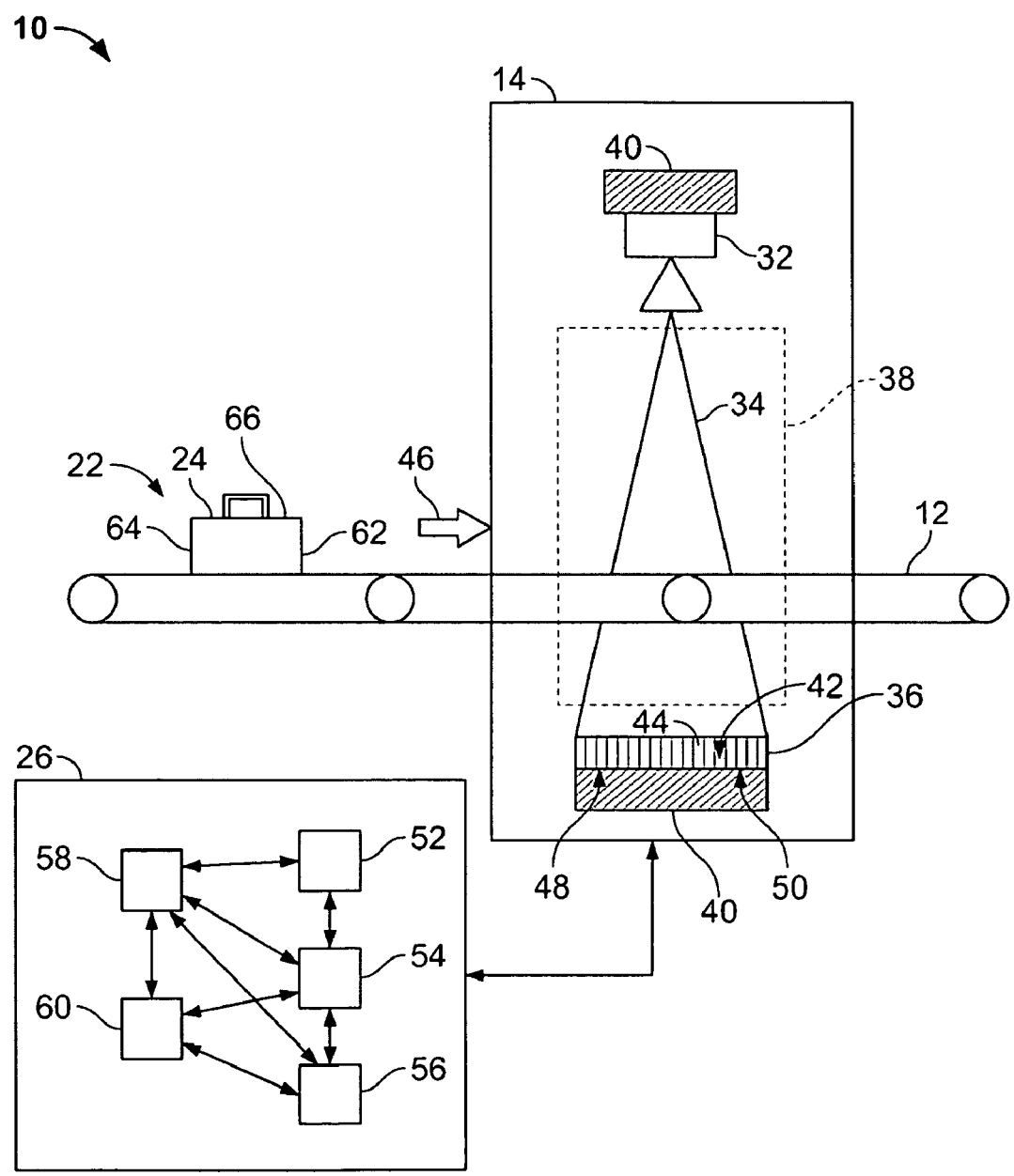

FIG. 2 is a schematic view of exemplary CT system 14 that may be used with scanning system 10 (shown in FIG. 1). CT system 14 includes a radiation source 32 for emitting radiation 34 and a detector 36 for detecting emitted radiation 34. An examination space 38 is defined between radiation source 32 and detector 36. In the exemplary embodiment, radiation source 32 and detector 36 are coupled to a gantry 40 for rotation about examination space 38. Alternatively, radiation source 32 and/or detector 36 are coupled within CT system 14 such that radiation source 32 and/or detector 36 are stationary with respect to examination space 38. In the exemplary embodiment, CT system 14 performs a continuous helical scan as stream 22 of objects 24 passes through examination space 38.

In the exemplary embodiment, control system 26 is in operational control communication with radiation source 32 and detector 36. Control system 26 controls emission of radiation 34 from radiation source 32 and receives data from detector 36 as described in more detail herein. Further, control system 26 controls components of CT system 14 in any suitable manner that enables CT system 14 to function as described herein. In the exemplary embodiment, radiation source 32 emits radiation 34 as X-rays in a cone-beam. Alternatively, radiation source 32 may emit any suitable radiation having any suitable beam shape, such as a fan beam.

Detector 36 includes a plurality of rows 42 and columns (not shown) of detector elements 44. Each row 42 extends in a direction that is substantially perpendicular to a direction of object travel as indicated by directional arrow 46 in FIG. 2. The columns are substantially parallel to the object travel direction indicated by directional arrow 46. Each detector element 44 produces an electrical signal that represents an intensity of an impinging radiation beam and, hence, the attenuation of the beam as the beam passes through object 24. The electrical signals produced by detector elements 44 are transmitted to control system 26.

In one embodiment, detector 36 is segmented into at least a first region 48 and a second region 50. First region 48 is upstream from second region 50 with respect to the direction of object travel as indicated by directional arrow 46. As such, first region 48 is in closer proximity to inlet 18 (shown in FIG. 1) of scanning system 10 than second region 50 is, and second region 50 is in closer proximity to outlet 20 (shown in FIG. 1) of scanning system 10 than first region 48 is. First region 48 is also referred to herein as a "leading edge region," and second region 50 is also referred to herein as a "trailing edge region." In the exemplary embodiment, first region 48 includes a predetermined number of rows 42, and second region 50 includes the same number of rows 42 as first region 48. Alternatively, first region 48 and second region 50 include different numbers of rows 42. In the exemplary embodiment, first region 48 and second region 50 each include at least one row 42. Detector 36 may also include rows 42 that are not in either first region 48 or in second region 50. It should be understood that detector 36 is not required to be segmented to detect a leading edge and a trailing edge as described herein. When detector 36 is not segmented, signals detected at any row and/or column of detector 36 are used to determine a leading edge and/or a trailing edge of object 24.

In the exemplary embodiment, control system 26 includes an object detection subsystem 52, an acquisition subsystem 54, and a reconstruction subsystem 56. Control system 26 also includes a memory 58 for data storage and a buffer 60 for temporary data storage. Although memory 58 and buffer 60 are shown as separate components, it should be understood that memory 58 and buffer 60 may be the same component within control system 26. Memory 58 and/or buffer 60 may be a random access memory (RAM) and/or a read only memory (ROM).

In the exemplary embodiment, object detection subsystem 52 is configured to determine a leading edge 62 and a trailing edge 64 of a first object 66 in stream 22 using radiation detected by detector 36, as described in more detail herein. Acquisition subsystem 54 is configured to process and/or record raw data of first object 66 based on the determination of leading edge 62 and trailing edge 64, and reconstruction subsystem 56 is configured to reconstruct an image of first object 66 using at least the processed and/or recorded raw data, as described in more detail herein.

Figure 3:
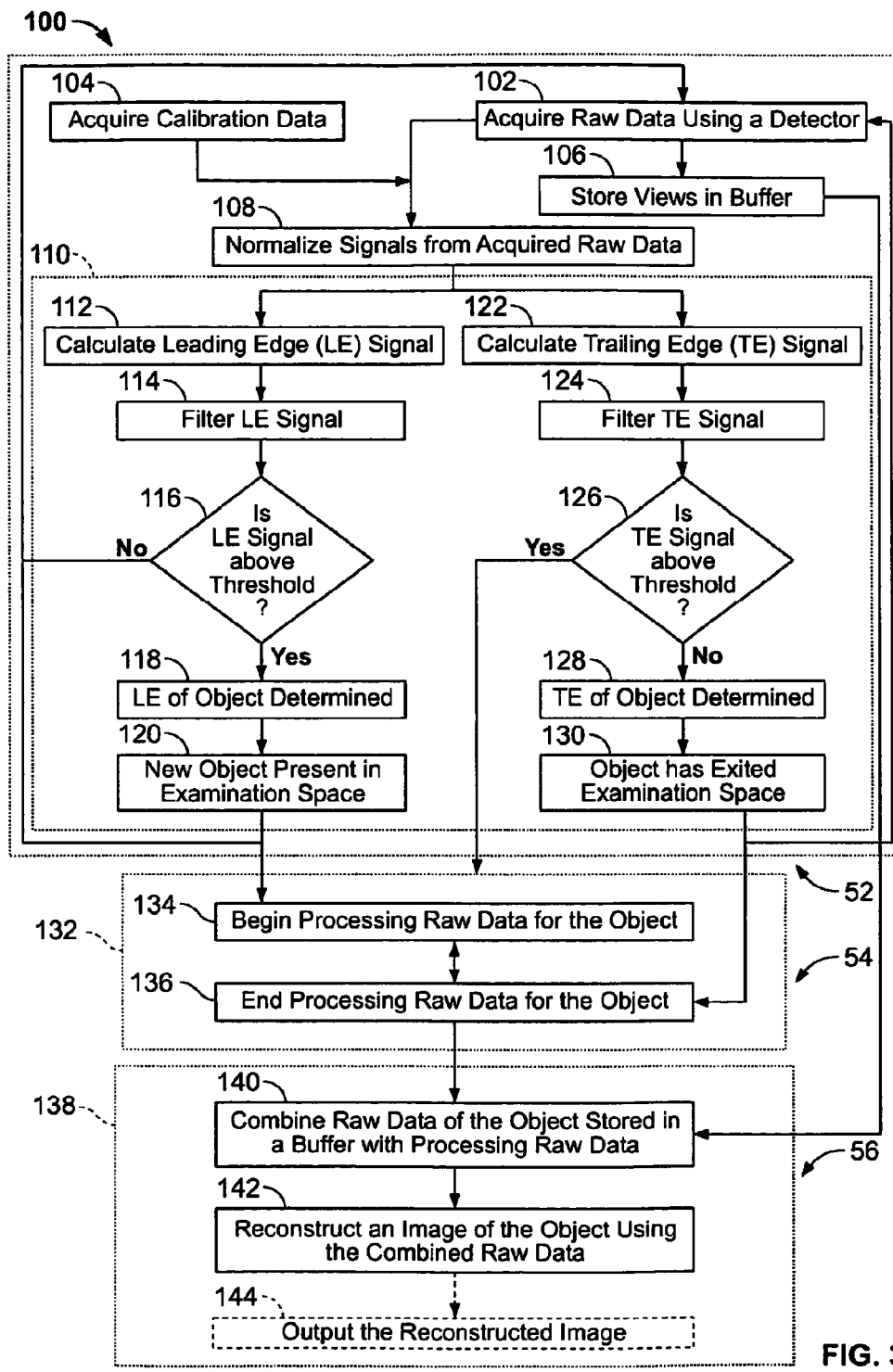

FIG. 3 is a flowchart of an exemplary method 100 for scanning a stream of objects that may be performed using scanning system 10 (shown in FIG. 1) and CT system 14 (shown in FIG. 2). In the exemplary embodiment, method 100 is used when stream 22 of objects 24 (shown in FIG. 1) is being scanned by CT system 14. In the exemplary embodiment, method 100 is performed by control system 26 (shown in FIGS. 1 and 2).

Method 100 includes continuously acquiring 102 raw data of stream 22 of objects 24 using CT system 14. More specifically, during normal operation of CT system 14, gantry 40 (shown in FIG. 2) is continuously rotating, and conveyor 12 (shown in FIG. 1) continuously transports objects 24 through examination space 38 (shown in FIG. 2) of CT system 14. As such, CT system 14 performs a continuous helical scan of stream 22 of objects 24 to acquire raw data of objects 24 using detector 36 (shown in FIG. 2). When no objects 24 are within examination space 38, CT system 14 acquires 104 calibration data from raw data acquired 102 without an object 24 present. Such a scan is referred to herein as an "air scan." Accordingly, the calibration data includes at least one reference value that includes a signature of conveyor 12, along with any other mechanical piece that is within a field of view of CT system 14.

In the exemplary embodiment, a suitable number of views are stored 106 in buffer 60 (shown in FIG. 2) before leading edge 62 (shown in FIG. 2) of first object 66 (shown in FIG. 2) is determined 110, as described in more detail below. More specifically, the views are temporarily stored 106 in buffer 60 such that an oldest view is replaced by a newest view. Storage 106 into buffer 60 continues on a temporary basis until leading edge 62 is determined 110. When leading edge 62 is determined 110, current views stored 106 in buffer 60 are stored in buffer 60 and/or memory 58 (shown in FIG. 2) without replacing any views until an image is reconstructed 138, as described in more detail below. As such, control system 26 can retroactively submit an earlier view and conveyor position as demarcating leading edge 62 of first object 66. Alternatively, method 100 does not include storing 106 views in buffer 60.

In the exemplary embodiment, signals of the acquired raw data are normalized 108 using the calibration data. More specifically, the signals are normalized 108 by accounting for components within examination space 38 other than objects 24, correcting for offset values, dividing by a gain signal for a corresponding view angle, and/or log normalizing. Once the signals are normalized 108, leading edge 62 and trailing edge 64 (shown in FIG. 2) of first object 66 are determined 110 from the raw data acquired 102 by detector 36.

To determine 110 leading edge 62, a leading edge signal within radiation detected at detector 36 is calculated 112. In the exemplary embodiment, the leading edge signal is calculated 112 by summing all signals generated from radiation received at detector 36. The calculated leading edge signal is filtered 114 using any suitable filtering method and/or technique. In the exemplary embodiment, filtering 114 the leading edge signal includes applying a temporal smoothing filter to the leading edge signal to facilitate reducing noise. The filtered leading edge signal is compared 116 to a threshold and/or a range. Examples of comparison 116 are described below. The threshold is any suitable threshold that indicates a change in intensity of the signals generated by detector 36 and/or the range is any suitable range that indicates a change in intensity of the signals generated by detector 36. In the exemplary embodiment, the threshold and/or range is selected such that normal noise in the signals does not indicate that leading edge 62 is present within examination space 38. In one embodiment, the threshold and/or range is selected empirically.

When the filtered leading edge signal is not above the threshold, raw data continues to be acquired 102 until a filtered leading edge signal is above the threshold. When the filtered leading edge signal is above the threshold, a presence of leading edge 62 of first object 66 at detector 36 is determined 118. Alternatively, when the filtered leading edge signal is above the threshold, raw data continues to be acquired 102 until a filtered leading edge signal is not above the threshold, and when the filtered leading edge signal is not above the threshold, a presence of leading edge 62 of first object 66 at detector 36 is determined 118. In an alternative embodiment, when the filtered leading edge signal is within the range, raw data continues to be acquired 102 until a filtered leading edge signal is not within the range, and when the filtered leading edge signal is not within the range, a presence of leading edge 62 of first object 66 at detector 36 is determined 118. Alternatively, when the filtered leading edge signal is not within the range, raw data continues to be acquired 102 until a filtered leading edge signal is within the range, and when the filtered leading edge signal is within the range, a presence of leading edge 62 of first object 66 at detector 36 is determined 118. In the exemplary embodiment, when the presence of leading edge 62 is determined 118, control system 26 determines 120 that first object 66 is a new object 24 present within examination space 38.

Similarly, trailing edge 64 of first object 66 is determined 110 by calculating 122 a trailing edge signal within the radiation detected at detector 36. In the exemplary embodiment, the trailing edge signal is calculated 122 by summing all signals generated from radiation received at detector 36. The calculated trailing edge signal is filtered 124 using any suitable filtering method and/or technique. In the exemplary embodiment, filtering 124 the trailing edge signal includes applying a temporal smoothing filter to the trailing edge signal to facilitate reducing noise. The filtered trailing edge signal is compared 126 to a threshold and/or a range. Examples of comparison 126 are described below. The threshold is any suitable threshold that indicates a change in intensity of the signals generated by detector 36, and/or the range is any suitable range that indicates a change in intensity of the signals generated by detector 36. In the exemplary embodiment, the threshold and/or range is selected such that normal noise in the signals does not indicate that trailing edge 64 is present within examination space 38. In one embodiment, the threshold and/or the range is selected empirically.

When the filtered trailing edge signal is not above the threshold, raw data continues to be processed 132, as described below, until a filtered trailing edge signal is above the threshold. As used herein, the term "process," "processing," and/or "processed" refers to a series of actions, procedures, mathematical manipulations, and/or activities that transforms acquired raw data into data that can be reconstructed into an image, which may include recording raw data to a memory, such as memory 58. When the filtered trailing edge signal is above the threshold, a presence of trailing edge 64 of first object 66 at detector 36 is determined 128. Alternatively, when the filtered leading edge signal is above the threshold, raw data continues to be processed 132 until a filtered leading edge signal is not above the threshold, and when the filtered leading edge signal is not above the threshold, a presence of trailing edge 64 of first object 66 at detector 36 is determined 128. In an alternative embodiment, when the filtered leading edge signal is within the range, raw data continues to be processed 132 until a filtered leading edge signal is not within the range, and when the filtered leading edge signal is not within the range, a presence of trailing edge 64 of first object 66 at detector 36 is determined 128. Alternatively, when the filtered leading edge signal is not within the range, raw data continues to be processed 132 until a filtered leading edge signal is within the range, and when the filtered leading edge signal is within the range, a presence of trailing edge 64 of first object 66 at detector 36 is determined 128. In the exemplary embodiment, when the presence of trailing edge 64 is determined 128, control system 26 determines 130 that first object 66 is not present within examination space 38, i.e., first object 66 has exited examination space 28. Accordingly, the trailing edge signal indicates the absence of a leading edge signal.

In the exemplary embodiment, comparison 116 and comparison 126 include comparing the calculated leading edge signals and the calculated trailing edge signals to reference values in the calibration data. More specifically, if comparison 116 and/or comparison 126 varies more than the threshold and/or the range from the reference values, leading edge 62 and/or trailing edge 64 is determined 110.

In a first example of comparison 116 and/or comparison 126, signal values from detector 36 are corrected for offset values (measured in the absence of radiation 34 (shown in FIG. 2)), and are then each subtracted from a corresponding signal in the calibration data. The correspondence between signals is based on an angular position of gantry 40 for a current view and for the air scan. When at least a subset of the detector signals exceeds a threshold above zero, first object 66 is determined to be present 120 or not present 130 within examination space 38, depending on whether leading edge signals or trailing edge signals are being compared 116 or 126, respectively.

In a second example of comparison 116 and/or comparison 126, signal values from detector 36 are transformed into a logarithm domain. As should be understood, reconstruction algorithms are applied to a log-normalized version of the signal values. The raw data is corrected for the offset values, divided by a gain signal for a corresponding view angle, and then log normalized. When at least a subset of the log normalized signal values exceeds a threshold above zero, first object 66 is determined to be present 120 or not present 130 in examination space 38, depending on whether leading edge signals or trailing edge signals are being compared 116 or 126, respectively.

In a third example of comparison 116 and/or comparison 126, detector values from either the first example or the second example are summed along regions of detector 36 to form a metric. When the metric exceeds a threshold, first object 66 is deemed present at a corresponding location with respect to detector 36.

Although three examples of comparison 116 and/or comparison 126 are set forth above, it should be understood that any other appropriate mathematical function can be applied to the detector data to determine the presence or the absence of first object 66 in examination space 38. Further, in the exemplary embodiment, determination of 110 leading edge 62 and trailing edge 64 is performed using all detector elements 44 (shown in FIG. 2) of detector 36 or a portion of detector elements 44 of detector 36. For example, in a particular embodiment, only signals generated from radiation 34 detected at first region 48 (shown in FIG. 2) and at second region 50 (shown in FIG. 2) are used to determine 110 leading edge 62 and trailing edge 64, respectively.

More specifically, radiation 34 detected at first region 48 is used to determine 118 leading edge 62, and radiation 34 detected at second region 50 is used to determine 128 trailing edge 64. In the exemplary embodiment, during normal operation of CT system 14, control system 26 monitors first region 48 for a leading edge signal, as described above in steps 112, 114, 116, 118, and 120. When the leading edge signal is determined 118, the current view and the conveyor position are processed and/or recorded to memory 58 as leading edge 62 for first object 66. Similarly, control system 26 monitors second region 50 for a trailing edge signal indicating the absence of the leading edge signal, as described above in steps 122, 124, 126, 128, and 130. When the leading edge signal is no longer determined 110, first object 66 has passed beyond examination space 38, and processing 132 of a data stream for first object 66 is ended 136.

In the exemplary embodiment, method 100 includes processing 132 acquired raw data of first object 66 based on the determined leading edge 62 and the determined trailing edge 64 using control system 26. More specifically, when the presence of first object 66 in examination space 38 is determined 120 by determining 118 leading edge 62, processing 132 of raw data is begun 134. In the exemplary embodiment, as long as the leading edge signal remains above the threshold and/or within the range, acquired raw data is processed 132. Further, because the trailing edge signal is similar to the leading edge signal, processing 132 continues until the trailing edge signal drops below the threshold and/or falls outside of the range. Processing 132 of the acquired raw data ends 136 when trailing edge 64 is determined 128. More specifically, in the exemplary embodiment, trailing edge 64 is determined 128 when the trailing edge signal drops below the threshold and/or falls outside of the range. Determination 128 of trailing edge 64 indicates that first object 66 is no longer present in examination space 38. A delay may be added after a time when trailing edge 64 is determined 128 such that the raw data continues to be processed 132 after trailing edge 64 has been determined 128. Such a delay facilitates ensuring that all views of first object 66 are processed 132. As such, by adding the delay to processing 132 of the acquired raw data, a plurality of views are processed 132 after trailing edge 64 is determined 128. Alternatively, the delay is not added to the processing 132 of raw data.

In the exemplary embodiment, after processing 132 of the raw data has ended 136, an image of first object 66 is reconstructed 138 using at least the recorded raw data. More specifically, the raw data processed 132 from when leading edge 62 was determined 118 to when trailing edge 64 was determined 128, with or without adding the delay, is reconstructed 138 using any suitable reconstruction algorithm. Further, in the exemplary embodiment, the plurality of views stored 106 in buffer 60 before leading edge 62 was determined 118 are combined 140 with the raw data processing 132 with first object 66 present in examination space 38, and the combined data are reconstructed 138 using any suitable reconstruction algorithm. As such, in a particular embodiment, the image of first object 66 is reconstructed 142 using the processed 132 raw data, the plurality of views stored 106 in buffer 60, and the plurality of views processed 132 during the time delay. The reconstructed image is optionally output 144 to display device 30 (shown in FIG. 1). The reconstructed image may also be transmitted to any suitable system for further processing and/or inspection. In the exemplary embodiment, the reconstructed image is used to determine contents of first object 66. In, for example, a transportation setting, such as an airport, the reconstructed image is used to determine if contraband is present within first object 66.

Method 100 is performed for each object 24 of stream 22 such that a data stream generated by CT system 14 is segmented according to whether an object 24 is present within examination space 38. More specifically, control system 26 only records and/or processes 132 raw data when object 24 is present within examination space 38 although CT system 14 continuously acquires 102 raw data regardless of the presence of object 24 in examination space 38. As such, method 100 gates the processing 132 of raw data and reconstruction 138 of an image depending on the presence of object 24. Accordingly, not all of the acquired raw data are reconstructed to determine the presence of object 24 in examination space 38 as is done in image space segmenting methods, which reduces computational time and cost of scanning system 10 as compared to scanning systems using image space segmenting methods.

The above-described embodiments facilitate determining extents of each object of an object stream by determining a leading edge and a trailing edge of each object. More specifically, determination of the leading edge and the trailing edge are performed using the CT system rather then an external system. By determining the leading edge and the trailing edge, the embodiments described herein enable data to be processed and reconstructed only when an object is present within an examination space of a CT system. Accordingly, the embodiments herein can use gaps in the stream of objects to reconstruct and/or process images of each object of the stream such that the above-described scanning system does not lose pace with the stream of objects. Further, because the embodiments described herein segment the acquired data stream before image reconstruction, rather than segmenting an image, computational time and cost is reduced as compared to scanning systems using image space segmenting methods. As such, the embodiments described herein enable selective reconstruction of images of objects, rather than requiring reconstruction of all acquired data.

The use of the above-described CT system to detect the leading edge and the trailing edge of an object has several technical advantages. One advantage is that the margins required around the leading edge and the trailing edge of the object can be chosen as small as possible. Such a selection allows for the smallest amount of data necessary to describe the object being processed and reconstructed by the scanning system described herein. As such, a theoretical maximum throughput of the scanning system is maximized.

In the above-described embodiments, the leading edge and trailing edge determination is made directly by the CT system using the signals measured on the detector. In one embodiment, the control system continuously monitors the detector data it receives. When the object being scanned enters into the scan region, it will create a signature signal change on the detector. For example, absorption of X-rays by the object will result in a drop in the number of detected photons on the detector. The control system monitors the detector for this drop in signal. When the control system detects the drop in signal, the control system marks the current data as indicative of the leading edge of the object. Buffering can be used to mark previous views as part of the object, if necessary. When the detector signal returns to the levels present when no object is in the scanner, the control system marks the current data as indicative of the trailing edge of the object and terminates processing of the data. Delays can be used to continue marking views as part of the object, if necessary. In an alternative embodiment, the control system monitors the detector in multiple sections. More specifically, detector rows that are furthest upstream are used to detect the leading edge of objects, and detector rows that are furthest downstream are used to detect the trailing edge of objects.

A technical effect of the systems and method described herein includes at least one of: (a) continuously acquiring raw data of the stream of objects using a computer tomography (CT) system; (b) determining a leading edge and a trailing edge of a first object of a stream of objects from raw data acquired by a detector by using a control system; (c) processing acquired raw data of a first object based on a determined leading edge and a determined trailing edge using a control system; and (d) reconstructing an image of a first object using at least processed raw data.

Exemplary embodiments of a method and systems for scanning a stream of objects are described above in detail. The method and systems are not limited to the specific embodiments described herein, but rather, components of systems and/or steps of the method may be utilized independently and separately from other components and/or steps described herein. For example, the method may also be used in combination with other imaging systems and methods, and is not limited to practice with only the computer tomography systems as described herein. Rather, the exemplary embodiment can be implemented and utilized in connection with many other imaging applications.

Although specific features of various embodiments of the invention may be shown in some drawings and not in others, this is for convenience only. In accordance with the principles of the invention, any feature of a drawing may be referenced and/or claimed in combination with any feature of any other drawing.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A method for scanning a stream of objects, said method comprising:

continuously acquiring raw data of the stream of objects using an X-ray system, the X-ray system including a detector;

calculating a leading edge signal and a trailing edge signal within radiation detected at the detector;

comparing the leading edge signal and the trailing edge signal to at least one threshold using a control system;

determining a leading edge and a trailing edge of a first object of the stream of objects based on results of the comparison using the control system;

processing acquired raw data of the first object based on the determined leading edge and the determined trailing edge using the control system; and reconstructing an image of the first object using at least the processed raw data.

2. A method in accordance with claim 1, wherein the detector includes a plurality of rows segmented into at least a first region and a second region, said determining a leading edge and a trailing edge of a first object of the stream of objects further comprises:
determining the leading edge of the first object using radiation detected at the first region of the detector; and
determining the trailing edge of the first object using radiation detected at the second region of the detector.

3. A method in accordance with claim 1, wherein comparing the leading edge signal and the trailing edge signal to at least one threshold further comprises:
filtering the leading edge signal;
comparing the filtered leading edge signal to the at least one threshold; and
determining a presence of the leading edge of the first object at the detector using results of the comparison of the filtered leading edge signal to the at least one threshold.

4. A method in accordance with claim 1, wherein comparing the leading edge signal and the trailing edge signal to at least one threshold further comprises:
filtering the trailing edge signal;
comparing the filtered trailing edge signal to the at least one threshold; and
determining a presence of the trailing edge of the first object at the detector using results of the comparison of the filtered trailing edge signal to the at least one threshold.

5. A method in accordance with claim 1, further comprising acquiring calibration data by performing a scan with no objects of the stream of objects in the X-ray system.

6. A method in accordance with claim 5, further comprising normalizing the raw data acquired by the detector using the calibration data.

7. A method in accordance with claim 6, wherein determining a leading edge and a trailing edge of a first object of the stream of objects further comprises determining the leading edge and the trailing edge of the first object using the normalized raw data.

8. A method in accordance with claim 1, wherein processing acquired raw data of the first object based on the determined leading edge and the determined trailing edge further comprises:
beginning the processing when the leading edge is determined; and
ending the processing when the trailing edge is determined.

9. A method in accordance with claim 1, further comprising:
storing a first plurality of views within a buffer of the control system before the leading edge is determined; and
adding a delay to the processing of the acquired raw data such that a second plurality of views are processed after the trailing edge is determined.

10. A method in accordance with claim 9, wherein reconstructing an image of the first object using at least the processed raw data further comprises reconstructing the image using the processed raw data, the first plurality of views, and the second plurality of views.

11. A scanning system, comprising:
a conveyor configured to transport a stream of objects through said scanning system; and
a computer tomography (CT) system configured to generate an image of a first object of the stream of objects, said CT system comprising a detector and a control system, said control system configured to:
calculate a leading edge signal and a trailing edge signal within radiation detected at said detector;
compare the leading edge signal and the trailing edge signal to at least one threshold;
determine a leading edge and a trailing edge of a first object of the stream of objects based on results of the comparison;
process raw data of the first object based on the determined leading edge and the determined trailing edge; and
reconstruct the image of the first object using at least the processed raw data.

12. A scanning system in accordance with claim 11, wherein said detector comprises a plurality of rows segmented into at least a first region and a second region, and said control system is further configured to:
determine the leading edge of the first object using radiation detected at said first region of said detector; and
determine the trailing edge of the first object using radiation detected at said second region of said detector.

13. A scanning system in accordance with claim 12, wherein said first region is in closer proximity to an inlet of said scanning system than said second region is.

14. A scanning system in accordance with claim 11, wherein said control system is configured to process raw data of the first object beginning when the leading edge is determined and ending when the trailing edge is determined.

15. A scanning system in accordance with claim 11, wherein said control system is further configured to:
filter the leading edge signal;
compare the filtered leading edge signal to the at least one threshold; and
determine a presence of the leading edge of the first object at said detector using results of the comparison of the filtered leading edge signal to the at least one threshold.

16. A scanning system in accordance with claim 15, wherein said control system is further configured to determine the presence of the first object within an examination space when the leading edge is determined.

17. A scanning system in accordance with claim 11, wherein said control system is further configured to:
filter the trailing edge signal;
compare the filtered trailing edge signal to the at least one threshold;
determine a presence of the trailing edge of the first object at said detector using results of the comparison of the filtered trailing edge signal to the at least one threshold; and
determine that the first object is not present within an examination space when the trailing edge is determined.

18. A computer tomography (CT) system, comprising:
a radiation source;
a detector configured to detect radiation emitted from said radiation source;
an examination space defined between said radiation source and said detector; and
a control system comprising:
an object detection subsystem configured to determine a leading edge and a trailing edge of a first object of a stream of objects by comparing a leading edge signal and a trailing edge signal calculated within radiation detected at said detector to at least one threshold;
an acquisition subsystem configured to process raw data of the first object based on the determined leading edge and the determined trailing edge; and a reconstruction subsystem configured to reconstruct an image of the first object using at least the processed raw data.

19. A CT system in accordance with claim 18, wherein said detector comprises a plurality of rows segmented into at least a first region and a second region, and said object detection subsystem is configured to:

determine the leading edge of the first object using radiation detected at said first region of said detector; and determine the trailing edge of the first object using radiation detected at said second region of said detector.

20. A CT system in accordance with claim 18, further comprising a gantry rotatable within said CT system, said radiation source and said detector coupled to said gantry for rotation about said examination space.

* * * * *